(12) United States Patent
Gupta et al.

(10) Patent No.: US 12,051,507 B2
(45) Date of Patent: Jul. 30, 2024

(54) SYSTEM AND METHOD FOR LEARNING DISENTANGLED REPRESENTATIONS FOR TEMPORAL CASUAL INFERENCE

(71) Applicant: Tata Consultancy Services Limited, Mumbai (IN)

(72) Inventors: Garima Gupta, Noida (IN); Lovekesh Vig, Noida (IN); Gautam Shroff, Noida (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 204 days.

(21) Appl. No.: 17/812,411

(22) Filed: Jul. 13, 2022

(65) Prior Publication Data
US 2023/0072173 A1 Mar. 9, 2023

(30) Foreign Application Priority Data
Jul. 16, 2021 (IN) .............................. 202121032201

(51) Int. Cl.
G16H 50/20 (2018.01)
G06N 5/04 (2023.01)

(52) U.S. Cl.
CPC .............. *G16H 50/20* (2018.01); *G06N 5/04* (2013.01)

(58) Field of Classification Search
None
See application file for complete search history.

(56) References Cited

U.S. PATENT DOCUMENTS

| | | |
|---|---|---|
| 2019/0030078 A1* | 1/2019 | Aliper .................. A61K 31/192 |
| 2020/0302297 A1* | 9/2020 | Jaganathan ........... G06F 18/213 |
| 2021/0265018 A1* | 8/2021 | Dutta ..................... G06N 3/048 |

FOREIGN PATENT DOCUMENTS

WO   WO2020206876 A1   10/2020

OTHER PUBLICATIONS

Hassanpour et al. ("Learning disentangled representations for counterfactual regression." International Conference on Learning Representations. 2019) (Year: 2019).*

(Continued)

*Primary Examiner* — Christopher B Tokarczyk
(74) *Attorney, Agent, or Firm* — FINNEGAN, HENDERSON, FARABOW, GARRETT & DUNNER LLP

(57) ABSTRACT

Existing techniques assume that all time varying covariates are confounding and thus attempts to balance a full state representation of a plurality of historical observants. The present disclosure processes a plurality of historical observants and treatment at a timestep t specific to each patient using an encoder network to a obtain a state representation $s_t$. A first set of disentangled representations comprising an outcome, a confounding and a treatment representation is learnt to predict an outcome $\hat{y}_{t+1}$. The first set of disentangled representations are concatenated to obtain a unified representation and the decoder network is initialized using the unified representation to obtain a state representation $s_{t+1}$. A second set of disentangled representations is learnt and concatenated to predict outcome $\hat{y}_{t+m+1}$ m+1 timesteps ahead of the timestep t and proceeding iteratively until m=τ−1.

15 Claims, 7 Drawing Sheets

(56) References Cited

OTHER PUBLICATIONS

Hassanpour, Negar et al., "Learning Disentangled Representations for CounterFactual Regression", Conference paper at ICLR, Date: 2019, Publisher: Open Review, https://openreview.net/attachment?id=HkxBJT4YvB&name=original_pdf.

Yang, Mengyue, et al., "CausalVAE: Disentangled Representation Learning via Neural Structural Causal Models", CVF Conference on Computer Vision and Pattern Recognition (CVPR), Date: 2021, Publisher: IEEE, https://openaccess.thecvf.com/content/CVPR2021/papers/Yang_CausalVAE_Disentangled_Representation_Learning_via_Neural_Structural_Causal_Models_CVPR_2021_paper.pdf.

Scholkopf, Bernhard et al., "Towards Causal Representation Learning", Machine Learning—Artificial Intelligence, Date: 2021, Publisher: Arxiv, https:/arxiv.org/pdf/2102.11107.pdf.

Rieckmann, A. et al., "Causes of Outcome Learning: A causal inference-inspired machine learning approach to disentangling common combinations of potential causes of a health outcome", International Journal of Epidemiology, Date: 2020, Publisher: medrxiv, https://www.medrxiv.org/content/10.1101/2020.12.10.20225243v2.full.pdf.

Ma, Jing et al., "Multi-Cause Effect Estimation with Disentangled Confounder Representation", Proceedings of the Thirtieth International Joint Conference on Artificial Intelligence, Date: 2021, Publisher: IJCAI, https:/www.ijcai.org/proceedings/2021/0384_pdf.

\* cited by examiner

SYSTEM AND METHOD FOR LEARNING DISENTANGLED REPRESENTATIONS FOR TEMPORAL CASUAL INFERENCE

PRIORITY CLAIM

This U.S. patent application claims priority under 35 U.S.C. § 119 to: India Application No. 202121032201, filed on Jul. 16, 2021. The entire contents of the aforementioned application are incorporated herein by reference.

TECHNICAL FIELD

This disclosure relates generally to the field of causal inferencing, and more particularly to a system and method for learning disentangled representations for temporal causal inference.

BACKGROUND

Causal inference refers to an intellectual discipline that considers the assumptions, study designs, and estimation strategies that allow researchers to draw causal conclusions based on data. Temporal causal inference aims to reveal the causal relationship among temporal variables and time series. Further accurate causal inference among time series helps to better understand the interactive scheme behind the temporal variables.

Critical medical decisions pertaining to a treatment plan selection for a patient require reasoning about potential future outcomes given the patient's current state and observed longitudinal clinical data. Further, medical professionals evaluating alternative treatment plans for the patient often encounter time varying confounders, or covariates that affect both the future treatment assignment and the outcome for the patient. A major hurdle in this endeavor is the presence of time-varying confounders, or patient covariates that are causally influenced by past treatments and further influence future treatments and outcomes.

One of the existing techniques attempt to address the problem of time-varying confounders for evaluation of treatment plans using Counterfactual Recurrent Network (CRN) which further uses a Gated Recurrent Unit (GRU) based recurrent model to predict potential future treatment effects by forcing hidden representations that can balance out time-varying confounding. However, these representations in existing techniques curtail the representation of covariates which influence both future treatment assignment and outcome prediction. Further, existing techniques have largely been focused on settings where the treatment and outcome depend only on a static snapshot of the covariates which include statistical techniques that employ reweighting of the data instances to balance the source and target distributions which while unbiased, are known to suffer from high variance.

As mentioned above, the standard randomized control trials, the most reliable technique for evaluating different treatment options, are often impractical in the temporal setting, as it may not be feasible to conduct a trial for every temporal variation of a particular treatment plan.

SUMMARY

Embodiments of the present disclosure present technological improvements as solutions to one or more of the above-mentioned technical problems recognized by the inventors in conventional systems. For example, in one embodiment, a method for learning disentangled representations for temporal causal inference is provided. The method includes processing, via one or more hardware processors, a plurality of historical observants $h_t$ and treatment $a_t$ at a timestep t specific to each patient i using an encoder network, wherein the encoder network comprises of a recurrent network with an LSTM (Long short-term memory) unit, wherein the plurality of historical observants $h_t$ for each patient i is derived from an observational dataset $D=\{\{x_t^i, a_t^i, y_{t+1}^i\}_{t=1}^T \cup \{v_i\}\}_{i=1}^N$ for N patients containing a plurality of time dependent patient covariates $x_t$ for each patient i, the treatment $a_t^i$ received by each patient i, corresponding response $y_{t+1}^i$ to the treatment $a_t^i$ obtained from each patient i and a plurality of static covariates v for each patient i and wherein, the plurality of historical observants $h_t$ is represented by a sequence of the patient's time-varying covariates $\bar{x}_{1,t-1}=[x_1, \ldots, x_{t-1}]$, a sequence of treatments $\bar{a}_{1,t-1}=[a_1, \ldots, a_{t-1}]$ and the plurality of static covariates v as $h_t=[\bar{x}_{1,t-1}, \bar{a}_{1,t-1}, v]$; obtaining, via the one or more hardware processors, a state representation $s_t$ using the processed plurality of historical observants $h_t$; learning, via the one or more hardware processors, a first set of disentangled representations comprising an outcome representation ($\Phi_Y^E(s_t)$), a confounding representation ($\Phi_\Delta^E(s_t)$) and a treatment representation ($\Phi_\Gamma^E(s_t)$) by passing the obtained state representation $s_t$ at each timestep t through a plurality of disentangled-two-layered Exponential Linear Unit (ELU) Multi-Layer Perceptrons (MLPs); passing, via the one or more hardware processors, the outcome representation ($\Phi_Y^E(s_t)$), the confounding representation ($\Phi_\Delta^E(s_t)$) and the treatment $a_t$ through a set of layers ($W_Y^E$) comprising the plurality of disentangled-two-layered Exponential Linear Unit (ELU) Multi-Layer Perceptron's (MLPs) at the timestep t to predict an outcome $\hat{y}_{t+1}$ one timestep ahead of the timestep t; concatenating, via the one or more hardware processors, the outcome representation ($\Phi_Y^E(s_t)$), the confounding representation ($\Phi_\Delta^E(s_t)$) and the treatment representation ($\Phi_\Gamma^E(s_t)$) from the encoder network to obtain a unified representation $\Psi_t$ for each timestep t for each patient i; initializing, via the one or more hardware processors, a state of a decoder network comprising a LSTM (Long short-term memory) unit using the unified representation $\Psi_t$ to obtain a state representation $s_{t+m}$ specific to each patient i m-timestep ahead of the timestep t, wherein the decoder network is trained by splitting the observational dataset D of trajectory of each patient i into shorter sequences of $\tau$ timestep represented as $\{\{\Psi_t\}\cup \hat{y}_{t+m}, a_{t+m}, \hat{y}_{t+m+1}\}_{m=1}^{\tau-1} \cup \{v\}_{t=1}^{T-\tau}$ and wherein, $\hat{y}_{t+m}$ denotes the predicted outcome m timestep ahead of the timestep t, $a_{t+m}$ denotes the treatment at each m timestep ahead of the timestep t and $\hat{y}_{t+m+1}$ denotes the predicted outcome m+1 timestep ahead of the timestep t; learning, via the one or more hardware processors, a second set of disentangled representations comprising an outcome representation ($\Phi_Y^D(s_{t+m})$), a confounding representation ($\Phi_\Delta^D(s_{t+m})$) and a treatment representation ($\Phi_\Gamma^D(s_{t+m})$) by passing the obtained state representation $s_{t+m}$ for each m timestep ahead of the timestep t through the plurality of disentangled-two-layered Exponential Linear Unit (ELU) Multi-Layer Perceptron's (MLPs); and concatenating, via the one or more hardware processors, the outcome representation ($\Phi_Y^D(s_{t+m})$), the confounding representation ($\Phi_\Delta^D(s_{t+m})$) and the treatment $a_{t+m}$ at each m timestep ahead of the timestep t and passing through a set of layers ($W_Y^D$) comprising the plurality of disentangled-two-layered Exponential Linear Unit (ELU) Multi-Layer Perceptron's (MLPs) to predict outcome $\widehat{y}_{t+m+1}$ m+1 timesteps ahead of the timestep t and proceeding iteratively for all values of m up to τ−1 ahead of the timestep t.

In another aspect, there is provided a system for learning disentangled representations for temporal causal inference. The system comprises: a memory storing instructions; one or more communication interfaces; and one or more hardware processors coupled to the memory via the one or more communication interfaces, wherein the one or more hardware processors are configured by the instructions to: process a plurality of historical observants $h_t$ and treatment $a_t$ at a timestep t specific to each patient i using an encoder network, wherein the encoder network comprises of a recurrent network with an LSTM (Long short-term memory) unit, wherein the plurality of historical observants $h_t$ for each patient i is derived from an observational dataset $D=\{\{x_t^i, a_t^i, y_{t+1}^i\}_{i=1}^{T^i} \cup \{v^i\}\}_{i=1}^{N}$ for N patients containing a plurality of time dependent patient covariates $x_t^i$ for each patient i, the treatment $a_t^i$ received by each patient i, corresponding response $y_{t+1}^i$ to the treatment $a_t^i$ obtained from each patient i and a plurality of static covariates v for each patient i and wherein, the plurality of historical observants $h_t$ is represented by a sequence of the patient's time-varying covariates $\overline{x}_{1,t-1}=[x_1, \ldots, x_{t-1}]$, a sequence of treatments $\overline{a}_{1,t-1}=[a_1, \ldots, a_{t-1}]$ and the plurality of static covariates v as $h_t=[\overline{x}_{1,t-1}, \overline{a}_{1,t-1}, v]$; The system further comprises obtaining a state representation $s_t$ using the processed plurality of historical observants $h_t$; learning a first set of disentangled representations comprising an outcome representation ($\Phi_\gamma^E(s_t)$), a confounding representation ($\Phi_\Delta^E(s_t)$) and a treatment representation ($\Phi_\Gamma^E(s_t)$) by passing the obtained state representation $s_t$ at each timestep t through a plurality of disentangled-two-layered Exponential Linear Unit (ELU) Multi-Layer Perceptrons (MLPs); passing the outcome representation ($\Phi_\gamma^E(s_t)$), the confounding representation ($\Phi_\Delta^E(s_t)$) and the treatment $a_t$ through a set of layers ($W_\gamma^E$) comprising the plurality of disentangled-two-layered Exponential Linear Unit (ELU) Multi-Layer Perceptron's (MLPs) at the timestep t to predict an outcome $\widehat{y}_{t+1}$ one timestep ahead of the timestep t; concatenating the outcome representation ($\Phi_\gamma^E(s_t)$), the confounding representation ($\Phi_\Delta^E(s_t)$) and the treatment representation ($\Phi_\Gamma^E(s_t)$) from the encoder network to obtain a unified representation $\Psi_t$ for each timestep t for each patient i; initializing a state of a decoder network comprising a LSTM (Long short-term memory) unit using the unified representation $\Psi_t$ to obtain a state representation $s_{t+m}$ specific to each patient i m-timestep ahead of the timestep t, wherein the decoder network is trained by splitting the observational dataset D of trajectory of each patient i into shorter sequences of τ timestep represented as $\{\{\Psi_t\} \cup \{y_{t+m}, a_{t+m}, y_{t+m+1}\}_{m=1}^{\tau-1} \cup \{v\}\}_{t=1}^{T-\tau}$ and wherein, $y_{t+m}$ denotes the predicted outcome m timestep ahead of the timestep t, $a_{t+m}$ denotes the treatment at each m timestep ahead of the timestep t and $\widehat{y}_{t+m+1}$ denotes the predicted outcome m+1 timestep ahead of the timestep t; learning a second set of disentangled representations comprising an outcome representation ($\Phi_\gamma^D(s_{t+m})$), a confounding representation ($\Phi_\Delta^D(s_{t+m})$) and a treatment representation ($\Phi_\Gamma^D(s_{t+m})$) by passing the obtained state representation $s_{t+m}$ for each m timestep ahead of the timestep t through the plurality of disentangled-two-layered Exponential Linear Unit (ELU) Multi-Layer Perceptron's (MLPs) and concatenating the outcome representation ($\Phi_\gamma^D(s_{t+m})$), the confounding representation ($\Phi_\Delta^D(s_{t+m})$) and the treatment $a_{t+m}$ at each m timestep ahead of the timestep t and passing through a set of layers ($W_\gamma^D$) comprising the plurality of disentangled-two-layered Exponential Linear Unit (ELU) Multi-Layer Perceptron's (MLPs) to predict outcome $\widehat{y}_{t+m+1}$ m+1 timesteps ahead of the timestep t and proceeding iteratively for all values of m up to τ−1 ahead of the timestep t.

In yet another aspect, there are provided one or more non-transitory machine-readable information storage mediums comprising one or more instructions which when executed by one or more hardware processors cause processing a plurality of historical observants $h_t$ and treatment $a_t$ at a timestep t specific to each patient i using an encoder network, wherein the encoder network comprises of a recurrent network with an LSTM (Long short-term memory) unit, wherein the plurality of historical observants $h_t$ for each patient i is derived from an observational dataset $D=\{\{x_t^i, a_t^i, y_{t+1}^i\}_{i=1}^{T^i} \cup \{v^i\}\}_{i=1}^{N}$ for N containing a plurality of time dependent patient covariates $x_t^i$ for each patient i, the treatment $a_t^i$ received by each patient i, corresponding response $y_{t+1}^i$ to the treatment $a_t^i$ obtained from each patient i and a plurality of static covariates v for each patient i and wherein, the plurality of historical observants $h_t$ is represented by a sequence of the patient's time-varying covariates $\overline{x}_{1,t-1}=[x_1, \ldots, x_{t-1}]$, a sequence of treatments $\overline{a}_{1,t-1}=[a_1, \ldots, a_{t-1}]$ and the plurality of static covariates v as $h_t=[\overline{x}_{1,t-1}, \overline{a}_{1,t-1}, v]$; obtaining a state representation $s_t$ using the processed plurality of historical observants $h_t$; learning a first set of disentangled representations comprising an outcome representation ($\Phi_\gamma^E(s_t)$), a confounding representation ($\Phi_\Delta^E(s_t)$) and a treatment representation ($\Phi_\Gamma^E(s_t)$) by passing the obtained state representation $s_t$ at each timestep t through a plurality of disentangled-two-layered Exponential Linear Unit (ELU) Multi-Layer Perceptrons (MLPs); passing the outcome representation ($\Phi_\gamma^E(s_t)$), the confounding representation ($\Phi_\Delta^E(s_t)$) and the treatment $a_t$ through a set of layers ($W_\gamma^E$) comprising the plurality of disentangled-two-layered Exponential Linear Unit (ELU) Multi-Layer Perceptron's (MLPs) at the timestep t to predict an outcome $\widehat{y}_{t+1}$ one timestep ahead of the timestep t concatenating the outcome representation ($\Phi_\gamma^E(s_t)$), the confounding representation ($\Phi_\Delta^E(s_t)$) and the treatment representation ($\Phi_\Gamma^E(s_t)$) from the encoder network to obtain a unified representation $\Psi_t$ for each timestep t for each patient i; initializing a state of a decoder network comprising a LSTM (Long short-term memory) unit using the unified representation $\Psi_t$ to obtain a state representation $s_{t+m}$ specific to each patient i m-timestep ahead of the timestep t, wherein the decoder network is trained by splitting the observational dataset D of trajectory of each patient i into shorter sequences of τ timestep represented as $\{\{\Psi_t\} \cup \{y_{t+m}, a_{t+m}, y_{t+m+1}\}_{m=1}^{\tau-1} \cup \{v\}\}_{t=1}^{T-\tau}$ and wherein, $y_{t+m}$ denotes the predicted outcome m timestep ahead of the timestep t, $a_{t+m}$ denotes the treatment at each m timestep ahead of the timestep t and $\widehat{y}_{t+m+1}$ denotes the predicted outcome m+1 timestep ahead of the timestep t; learning a second set of disentangled representations comprising an outcome representation ($\Phi_\gamma^D(s_{t+m})$), a confounding representation ($\Phi_\Delta^D(s_{t+m})$) and a treatment representation ($\Phi_\Gamma^D(s_{t+m})$) by passing the obtained state representation $s_{t+m}$ for each m timestep ahead of the timestep t through the plurality of disentangled-two-layered Exponential Linear Unit (ELU) Multi-Layer Perceptron's (MLPs) and concatenating the outcome representation ($\Phi_\gamma^D(s_{t+m})$), the confounding representation ($\Phi_\Delta^D(s_{t+m})$) and the treatment $a_{t+m}$ at each m timestep ahead of the timestep t and passing through a set of layers ($W_\gamma^D$) comprising the plurality of disentangled-two-layered Exponential Linear Unit (ELU) Multi-Layer Perceptron's (MLPs) to predict outcome $\hat{y}_{t+m+1}$ m+1 timesteps ahead of the timestep t and proceeding iteratively for all values of m up to τ−1 ahead of the timestep t.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
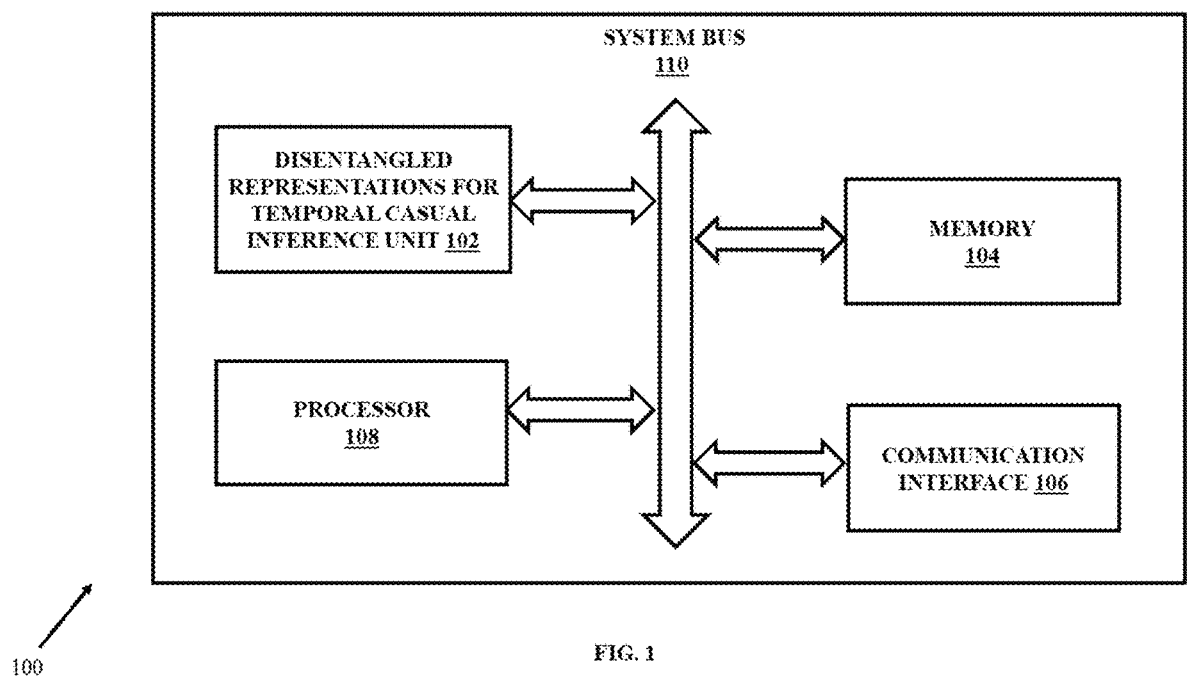
FIG. 1 illustrates an exemplary system, for learning disentangled representations for temporal causal inference, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

The present disclosure provides a system and method for learning disentangled representations for temporal causal inference. The existing techniques assumes that all time varying covariates are confounding and thus attempt to balance the full state representation. In reality, a subset of covariates may in fact be confounding and in general unknown and one of the recent works on counterfactual estimation in the static, non-temporal setting has suggested that disentangling the covariate representation into separate factors, where each factor either influence treatment selection, patient outcome or both can help isolate selection bias and restrict balancing efforts to factors that influence outcome, allowing the remaining factors which predict treatment without needlessly being balanced. The present disclosure proposes Disentangled Representations for Temporal Causal Inference (DRTCI), a system for temporal causal inference. The proposed Disentangled Representations for Temporal Causal Inference (DRTCI) system uses a recurrent neural network to learn hidden representation of the patient's evolving covariates that disentangles into three representations. Further each of the three representations causally determine either treatment, outcome or both treatment and outcome.

Referring now to the drawings, and more particularly to FIG. 1 through FIG. 6, where similar reference characters denote corresponding features consistently throughout the figures, there are shown preferred embodiments and these embodiments are described in the context of the following exemplary system and/or method.

FIG. 1 illustrates an exemplary system, for learning disentangled representations for temporal causal inference, in accordance with some embodiments of the present disclosure. The system 100 includes a disentangled representations for temporal causal inference unit 102 for learning disentangled representations for temporal causal inference, in accordance with some embodiments of the present disclosure. The disentangled representations for temporal causal inference unit 102 include or is otherwise in communication with a memory 104, a communication interface 106, and a processor 108. The memory 104, the communication interface 106, and the processor 108 may be coupled by a system bus 110 or a similar mechanism. Although FIG. 1 shows example components of the disentangled representations for temporal causal inference unit 102, in other implementations, the system 100 may contain fewer components, additional components, different components, or differently arranged components than depicted in FIG. 1.

The processor 108 may be implemented as one or more microprocessors, microcomputers, microcontrollers, digital signal processors, central processing units, state machines, logic circuitries, and/or any devices that facilitates in designing polymeric carrier for controlled release of molecules. Further, the processor 108 may comprise a multi-core architecture. Among other capabilities, the processor 108 is configured to fetch and execute computer-readable instructions or modules stored in the memory 104. The processor 108 may include circuitry implementing, among others, audio and logic functions associated with the communication. For example, the processor 108 may include, but are not limited to, one or more digital signal processors (DSPs), one or more microprocessor, one or more special-purpose computer chips, one or more field-programmable gate arrays (FPGAs), one or more application-specific integrated circuits (ASICs), one or more computer(s), various analog to digital converters, digital to analog converters, and/or other support circuits. The processor 108 thus may also include the functionality to encode messages and/or data or information. The processor 108 may include, among other things, a clock, an arithmetic logic unit (ALU) and logic gates configured to support operation of the processor 108. Further, the processor 108 may include functionality to execute one or more software programs, which may be stored in the memory 104 or otherwise accessible to the processor 108.

The memory 104, may store any number of pieces of information, and data, used by the system 100 to implement the functions of the system 100. The memory 104 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes. Examples of volatile memory may include but are not limited to volatile random-access memory (RAM). The non-volatile memory may additionally or alternatively comprise an electrically erasable programmable read only memory (EEPROM), flash memory, hard drive, or the like. The memory 104 may be configured to store information, data, applications, instructions, or the like for enabling the system 100 to carry out various functions in accordance with various example embodiments. Additionally, or alternatively, the memory 104 may be configured to store instructions which when executed by the processor 108 causes the system 100 to behave in a manner as described in various embodiments.

The communication interface(s) 106 can facilitate multiple communications within a wide variety of networks and protocol types, including wired networks, for example, local area network (LAN), cable, etc., and wireless networks, such as Wireless LAN (WLAN), cellular, or satellite. For the purpose, the communication interface (s) 106 may include one or more ports. One or more functionalities of the system 100 and components thereof, is further explained in detail with respect to block diagram described in FIG. 2.

Figure 2:
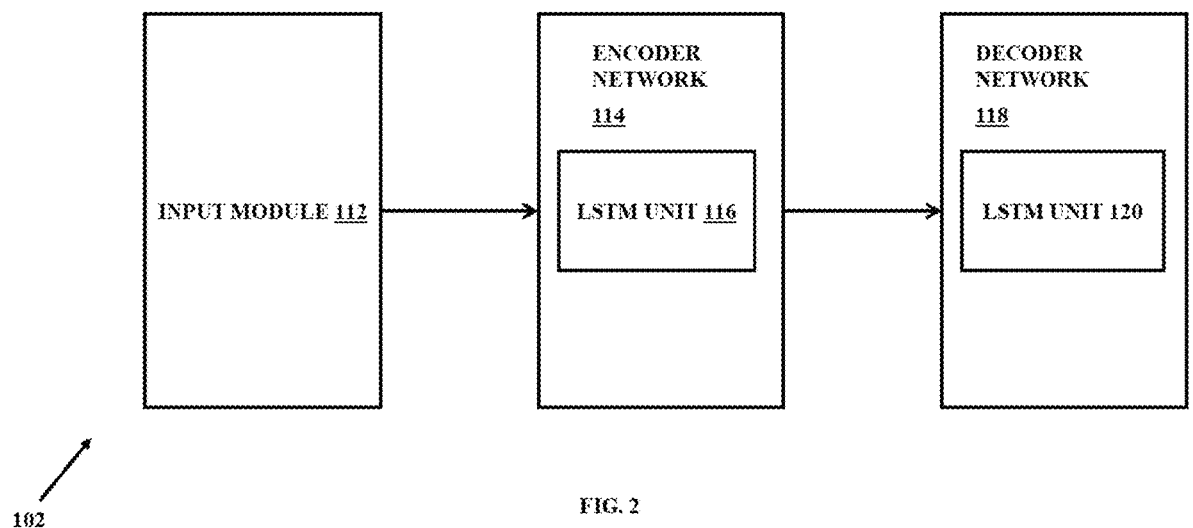
FIG. 2 is a functional block diagram of the system for learning disentangled representations for temporal causal inference according to some embodiments of the present disclosure.

FIG. 2 is a functional block diagram of the system for learning disentangled representations for temporal causal inference according to some embodiments of the present disclosure. In an embodiment, the disentangled representations for temporal causal inference unit 102 comprises of various modules that include an input module 112, an encoder network 114 and a decoder network 118. The encoder network 114 further incudes a LSTM (Long short-term memory) unit 116 and the decoder network 118 further includes a LSTM (Long short-term memory) unit 120.

Figure 3A:
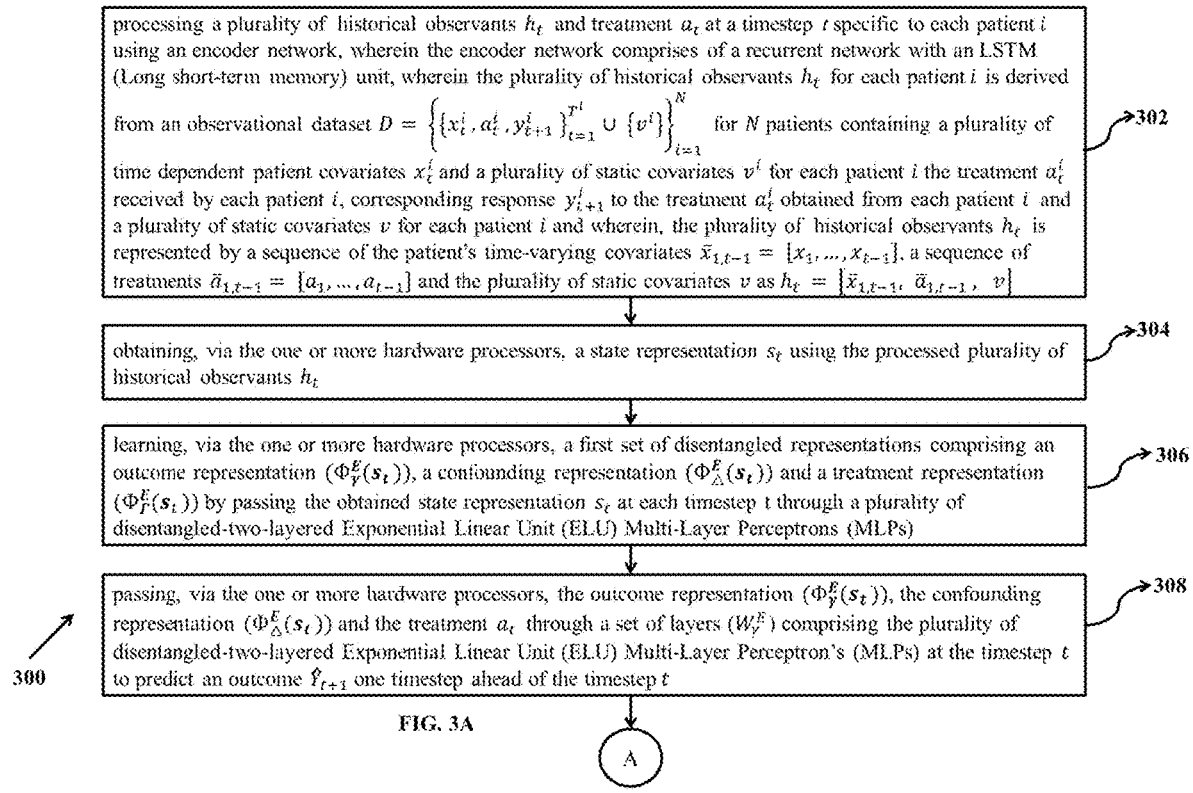
FIGS. 3A and 3B shows an exemplary flow diagram illustrating a method learning disentangled representations for temporal causal inference, in accordance with some embodiments of the present disclosure.
Figure 3B:
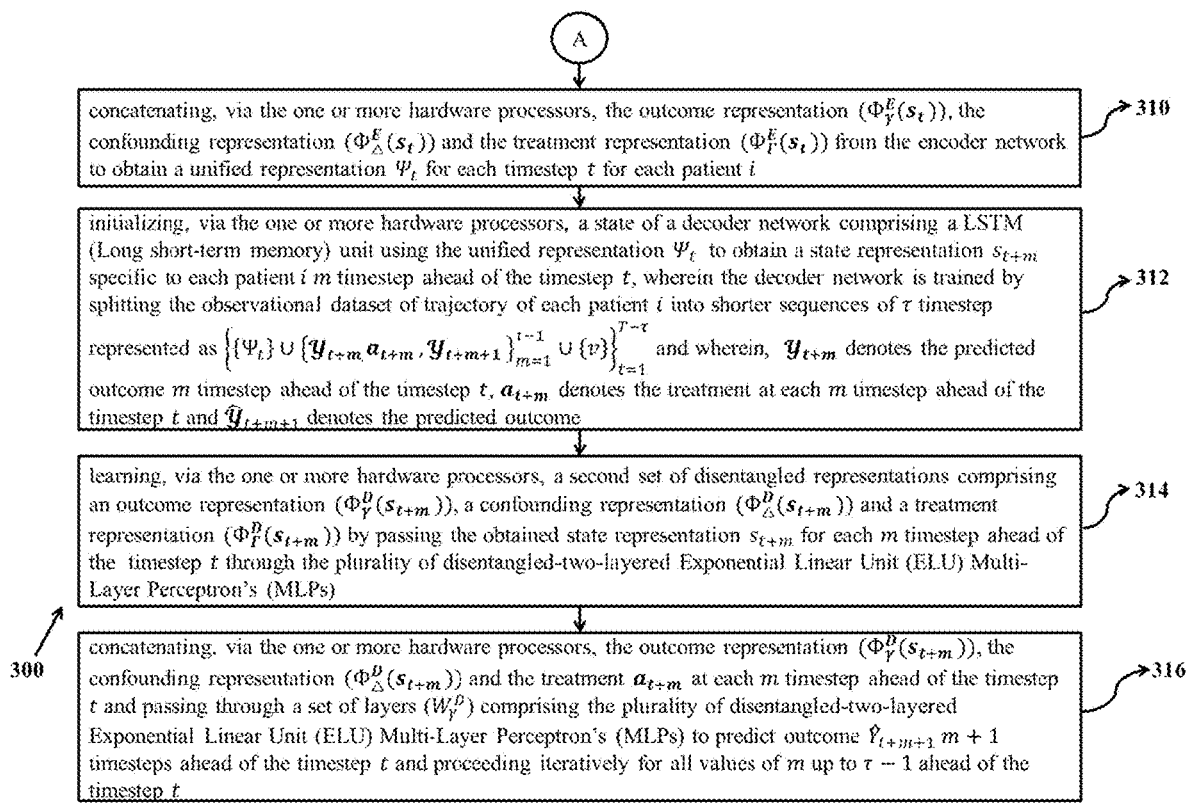

FIGS. 3A and 3B, with reference to FIGS. 1-2, is an exemplary flow diagram 300 illustrating a method for learning disentangled representations for temporal causal inference using the system 100 of FIG. 1 according to some embodiments of the present disclosure. In an embodiment, the system 100 comprises one or more data storage devices or the memory 104 operatively coupled to the one or more processors 108 and is configured to store instructions for execution of steps of the method by the disentangled representations for temporal causal inference unit 102. The steps of the method of the present disclosure will now be explained with reference to the components of the system 100 and the steps 302-316 as depicted in FIGS. 1-2, and the flow diagram as depicted in FIGS. 3A and 3B.

Operations of the flowchart, and combinations of operation in the flowchart, may be implemented by various means, such as hardware, firmware, processor, circuitry and/or other device associated with execution of software including one or more computer program instructions. For example, one or more of the procedures described in various embodiments may be embodied by computer program instructions. In an example embodiment, the computer program instructions, which embody the procedures, described in various embodiments may be stored by at least one memory device of a system and executed by at least one processor in the system. Any such computer program instructions may be loaded onto a computer or other programmable system (for example, hardware) to produce a machine, such that the resulting computer or other programmable system embody means for implementing the operations specified in the flowchart. It will be noted herein that the operations of the method 300 are described with help of system 102. However, the operations of the method 300 can be described and/or practiced by using any other system.

The disclosed method 300 relates to the learning of disentangled representations for temporal causal inference. At step 302 of the method, the one or more hardware processors 108 process a plurality of historical observants $h_t$ and treatment $a_t$ at a timestep t specific to each patient i using an encoder network 114 (FIG. 2). The encoder network 114 (FIG. 2) comprises of a recurrent network with an LSTM (Long short-term memory) unit 116. The plurality of historical observants $h_t$ for each patient i is derived from an observational dataset $D=\{\{x_t^i, a_t^i, y_{t+1}^i\}_{i=1}^T \cup \{v^i\}\}_{i=1}^N$ for N patients containing a plurality of time dependent patient covariates $x_t^i$ for each patient i, the treatment $a_t^i$ received by each patient i, corresponding response $y_{t+1}^i$ to the treatment $a_t^i$ obtained from each patient i and a plurality of static covariates v for each patient i and wherein the plurality of historical observants $h_t$ is represented by a sequence of the patient's time-varying covariates $\bar{x}_{1,t-1}=[x_1, \ldots, x_{t-1}]$, a sequence of treatments $\bar{a}_{1,t-1}=[a_1, \ldots, a_{t-1}]$ and the plurality of static covariates v as $h_t=[\bar{x}_{1,t-1}, \bar{a}_{1,t-1}, v]$. In an embodiment of the present disclosure, the input module 112 of FIG. 2 is configured to receive inputs related to the plurality of historical observants $h_t$ comprising of patient's history and covariates from a domain database. The encoder network 114 of FIG. 2 is configured to process the received plurality of historical observants $h_t$ further to obtain state representation $s_t$ as mentioned above. The LSTM unit 116 of encoder network 114 and the LSTM unit 120 of decoder network 118 of FIG. 2 are a part of recurrent unit (comprised in encoder network 114 and decoder network 118) respectively which are used to represent the variable length history to a fixed length state vector. At step 304 of the method, the one or more hardware processors 108, obtain a state representation $s_t$ using the processed plurality of historical observants $h_t$. The present disclosure employs a recurrent neural network (comprised in the memory 104 and invoked for execution to perform steps described herein) to map the plurality of historical observants $h_t$ comprising of the (variable-length) patient history $h_t$ and covariates $x_t$ at the timestep t to a latent, fixed length state representation $s_t$ which is represented as:

$$s_t = f_{t,s}(h_t, x_t) \qquad (1)$$

At step 306 of the method, the one or more hardware processors 108, learn a first set of disentangled representations comprising an outcome representation ($\Phi_Y^E(s_t)$), a confounding representation ($\Phi_\Delta^E(s_t)$) and a treatment representation ($\Phi_\Gamma^E(s_t)$) by passing the obtained state representation $s_t$ at each timestep t through a plurality of disentangled-two-layered Exponential Linear Unit (ELU) Multi-Layer Perceptrons (MLPs). The present disclosure and the system and method described herein learn three disentangled representations of the latent state representation $s_t$ at timestep t which includes the outcome representation ($\Phi_Y^E(s_t)$) which affects future outcome $\mathcal{Y}_{t+1}$, the confounding representation ($\Phi_\Delta^E(s_t)$) which affects both future treatment assignment and outcome $\mathcal{Y}_{t+1}$ and the treatment representation ($\Phi_\Gamma^E(s_t)$) which affects the treatment assignment $a_t$. All of the above representations are learnt in a disengaged manner which is explained in later sections. The three disentangled representations are learned by passing the representation $s_t$ at the timestep t through the three disentangled two-layered ELU Multi-Layer perceptron's (MLPs) which includes $\Phi_Y(\bullet)$, $\Phi_\Delta(\bullet)$, $\Phi_\Gamma(\bullet)$, parameters of which are learned using a set of loss functions namely a prediction loss, a treatment loss, an imbalance loss, and a weighting loss. The details of the loss functions are described as below:

Prediction Loss and Weighting Loss:

The concatenation of the confounding representation, the outcome representation, and the treatment at the timestep t is passed to a regression arm ($W_\gamma$) comprising of MLP-ELU-MLP layers to predict outcome $\hat{y}_{t+1}$.

$$\hat{y}_{t+1} = W_\gamma([\Phi_\gamma^E(s_t), \Phi_\Delta^E(s_t), a_t]) \quad (2)$$

The present disclosure uses a squared error loss for learning the parameters of the confounding representation and the outcome representation. However, since the objective of the present disclosure is to predict factual as well as counterfactual outcome while the observational dataset D contains only factual outcomes, an importance weighting of squared error is used to emphasize those instances that are more useful for the prediction of the counterfactual outcomes. The aforementioned importance weight is an extension of binary treatment importance weighting introduced to K treatments which is represented as below:

$$\omega_t = \sum_{k=1}^{K} \frac{p(\Phi_\Delta^E(s_t)|A_k)}{p(\Phi_\Delta^E(s_t)|a_t)} = \sum_{k=1}^{K} \frac{p(a_t)}{p(A_k)} \frac{p(A_k|\Phi_\Delta^E(s_t))}{p(a_t|\Phi_\Delta^E(s_t))} \quad (3)$$

In the above equation (3) $p(a_t)$, $p(A_k)$ are the marginal probabilities for factual treatment $a_t$ and treatment option $A_k$ respectively and are computed from the observational dataset D. Further propensity $p(A_k|\Phi_\Delta^E(s_t))$ is obtained by passing $\Phi_\Delta^E(s_t)$ via an $W_\Delta(\cdot)$ (MLP and a soft max layer) with $\mathcal{L}_{t,W}$ weighting loss as: $\mathcal{L}_{t,W}(W_\Delta, \Phi_\Delta) = -\Sigma_{k=1}^{K} a_t(k)\log(p(A_k|\Phi_\Delta^E(s_t)))$. The weighted square error is then used as outcome regression loss ($\mathcal{L}_{t,P}$) as: $\mathcal{L}_{t,P}(\Phi_\Delta, \Phi_\gamma, W_\gamma) = \omega_t (y_{t+1} - \hat{y}_{t+1})^2$.

Treatment Loss:

The treatment loss is employed for learning the logging policy that guides the treatment assignment. For this, both the confounding representation $\Phi_\Delta^E(s_t)$ and the treatment representation ($\Phi_\Gamma^E(s_t)$) are passed through $W_\Gamma(\cdot)$ (MLP and the softmax layer) to learn the propensity of treatment. The treatment loss ($\mathcal{L}_{t,T}$) is then used for learning the weights of the confounding representation and the treatment representation as:

$$\mathcal{L}_{t,T}(\Phi_\Delta, \Phi_\Gamma, W_\Gamma) = -\Sigma_{k=1}^{K} a_t(k)\log(p(A_k|[\Phi_\Delta^E(s_t), \Phi_\Gamma^E(s_t)])) \quad (4)$$

Imbalance Loss:

To overcome the bias due to the time-varying confounders, the proposed disclosure uses an adversarial imbalance loss ($\mathcal{L}_{t,I}$): $\mathcal{L}_{t,I}(\Phi_\gamma) = -\Sigma_{k=1}^{K} a_t(k)\log(p(A_k|\Phi_\gamma^E(s_t)))$ which ensures that the outcome representation $\Phi_\gamma(s_t)$ is not predictive of treatment assignment, i.e., $p(\Phi_\gamma^E(s_t)|A_1) = \ldots = p(\Phi_\gamma^E(s_t)|A_K)$. The system 100 computes propensity $p(A_k|\Phi_\gamma^E(s_t))$ by passing outcome representation via randomly initialized fixed weight one-layer MLP followed by the softmax layer. It is to be noted that the present disclosure uses shorthand $p_1(s_t)$, $p_2(s_t)$, $p_3(s_t)$ for propensities $p(A_k|\Phi_\Delta^E(s_t))$, $p(A_k|[\Phi_\Delta^E(s_t), \Phi_\Gamma^E(s_t)])$, $p(A_k|\Phi_\gamma^E(s_t))$.

At step 308 of the method 300, the one or more hardware processors 108, pass the outcome representation ($\Phi_\gamma^E(s_t)$), the confounding representation ($\Phi_\Delta^E(s_t)$) and the treatment $a_t$ through a set of layers ($W_\gamma^E$) comprising the plurality of disentangled-two-layered Exponential Linear Unit (ELU) Multi-Layer Perceptron's (MLPs) at the timestep t to predict an outcome $\hat{y}_{t+1}$ one timestep ahead of the timestep t. At step 310 of the method 300, the one or more hardware processors 108, concatenate the outcome representation ($\Phi_\gamma^E(s_t)$), the confounding representation ($\Phi_\Delta^E(s_t)$) and the treatment representation ($\Phi_\Gamma^E(s_t)$) from the encoder network 114 to obtain a unified representation $\Psi_t$ for each timestep t for each patient i. In an embodiment of the present disclosure, the decoder network 118 is used for extending next time step prediction to multiple (m) timesteps ahead of the timestep t. At step 312 of the method 300, the one or more hardware processors 108, initialize a state of a decoder network 118 comprising a LSTM (Long short-term memory) unit 120 using the unified representation $\Psi_t$ to obtain a state representation $s_{t+m}$ specific to each patient i, m-timestep ahead of the timestep t. The decoder network 118 is trained by splitting the observational dataset D of trajectory of each patient i into shorter sequences of $\tau$ timestep represented as $\{\{\Psi_t\} \cup \{y_{t+m}, a_{t+m}, \hat{y}_{t+m+1}\}_{m=1}^{\tau-1} \cup \{v\}\}_{t=1}^{T-\tau}$ wherein $\hat{y}_{t+m}$ denotes the predicted outcome m timestep ahead of the timestep t, $a_{t+m}$ denotes the treatment at each m timestep ahead of the timestep t and $\hat{y}_{t+m+1}$ denotes the predicted outcome m+1 timestep ahead of the timestep t. At step 314 of the method 300, the one or more hardware processors 108, learn a second set of disentangled representations comprising an outcome representation ($\Phi_\gamma^D(s_{t+m})$), a confounding representation ($\Phi_\Delta^D(s_{t+m})$) and a treatment representation ($\Phi_\Gamma^D(s_{t+m})$) by passing the obtained state representation $s_{t+m}$ for each m timestep ahead of the timestep t through the plurality of disentangled-two-layered Exponential Linear Unit (ELU) Multi-Layer Perceptron's (MLPs). At step 316 of the method 300, the one or more hardware processors 108, concatenate the outcome representation ($\Phi_\gamma^D(s_{t+m})$), the confounding representation ($\Phi_\Delta^D(s_{t+m})$) and the treatment $a_{t+m}$ at each m timestep ahead of timestep t and passing through a set of layers ($W_\gamma^D$) comprising the plurality of disentangled-two-layered Exponential Linear Unit (ELU) Multi-Layer Perceptron's (MLPs) to predict outcome $\hat{y}_{t+m+1}$ m+1 timesteps ahead of the timestep t and proceeding iteratively for all values of m up to $\tau-1$ ahead of the timestep t.

Figure 4:
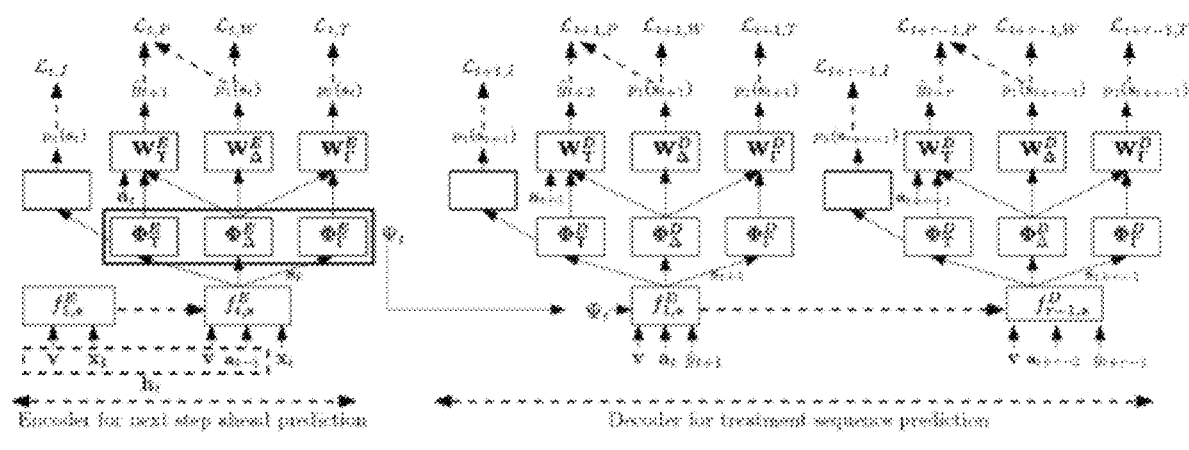
FIG. 4 illustrates an architecture for learning disentangled representations for temporal causal inference, in accordance with some embodiments of the present disclosure.

FIG. 4 illustrates an architecture for learning disentangled representations for temporal causal inference, in accordance with some embodiments of the present disclosure. The encoder network 114 uses a recurrent network with the LSTM unit 116 to process the plurality of historical observants $h_t$ and covariates $x_t$ at timestep t to obtain state representation $s_t$ (represented in Eq. 1). Further, the state representation $s_t$ is disentangled into the first set of disentangled representations comprising the outcome representation ($\Phi_\gamma^E(s_t)$), the confounding representation ($\Phi_\Delta^E(s_t)$), and the treatment representation ($\Phi_\Gamma^E(s_t)$) using the loss at timestep t as $$\mathcal{L}_t(\Phi_\Delta^E, \Phi_\gamma^E, \Phi_\Gamma^E, W_\Delta^E, W_\gamma^E, W_\Gamma^E; \beta) = \mathcal{L}_{t,P}(\Phi_\Delta^E, \Phi_\gamma^E, W_\gamma^E) + \mathcal{L}_{t,T}(\Phi_\Delta^E, \Phi_\Gamma^E, W_\Gamma^E) + \mathcal{L}_{t,P}(W_\Delta^E, \Phi_\Delta^E) - \beta \mathcal{L}_{t,I}(\Phi_\gamma^E) \quad (5)$$

where $\beta$ is obtained using hyperparameter tuning which is described in later sections and superscript E stands for one or more parameters pertaining to the encoder network 114. The one or more parameters of the encoder network 114 comprises of weights of LSTM unit, weights of Exponential Linear Unit (ELU) and weights of Multi-Layer Perceptron's (MLP's) wherein, weights of LSTM unit, weights of Exponential Linear Unit (ELU) and weights of Multi-Layer Perceptron's (MLP's). The outcome representation ($\Phi_\gamma^E(s_t)$), the confounding representation ($\Phi_\Delta^E(s_t)$), and the treatment representation ($\Phi_\Gamma^E(s_t)$) at the timestep t are then used to forecast the outcome at the next timestep $\hat{\mathcal{Y}}_{t+1}$ as described in equation 2. The present disclosure uses a sequence-to-sequence architecture as depicted in FIG. 4, which extends the next timestep ahead outcome prediction using the encoder network 114 to a τ-step ahead prediction using the decoder network 118. the encoder network 114 is learned first, then the decoder network 118 is updated as described in the following section.

In the present disclosure, the disentangled representations from the encoder network 114 are concatenated to obtain a unified representation $\Psi_t = \Phi_\gamma^E(s_t) \oplus \Phi_\Delta^E(s_t) \oplus \Phi_\Gamma^E(s_t)$. The representation $\Psi_t$ is obtained for each timestep for N patients. The observational dataset D is processed by splitting trajectory of each patient i into shorter sequences of T timesteps which is represented as $\{\{\Psi_t\} \cup \{\mathcal{Y}_{t+m}, a_{t+m}, \mathcal{Y}_{t+m+1}\}_{m=1}^{\tau-1} \cup \{v\}\}_{t=1}^{T-\tau}$ for training the decoder network 118. The representation $\Psi_t$ is used to initialize the state of the decoder network 118 and to finally obtain a state representation for the patient m-timesteps in the future which is represented as:

$$s_{t+m} = f_{m,s}^D([v, \mathcal{Y}_{t+m}, a_{t+m-1}]) \quad (6)$$

where inputs to the LSTM unit 120 of the decoder network 118 are static covariates v, previous timestep's outcome $\mathcal{Y}_{t+m}$ and previous treatment $a_{t+m-1}$ with superscript D pertaining to one or more parameters of the decoder network 118. The one or more parameters of the decoder network 118 comprises of weights of LSTM unit, weights of Exponential Linear Unit (ELU) and weights of Multi-Layer Perceptron's (MLP's) wherein, weights of LSTM unit, weights of Exponential Linear Unit (ELU) and weights of Multi-Layer Perceptron's (MLP's). The state representation ($s_{t+m}$) is further disentangled into the second set of disentangled representations comprising the confounding representation ($\Phi_\Delta^D(s_{t+m})$), the treatment representation ($\Phi_\Gamma^D(s_{t+m})$), and the outcome representation ($\Phi_\gamma^D(s_{t+m})$), using $\mathcal{L}_{t+m}(\Phi_\Delta^D, \Phi_\gamma^D, \Phi_\Gamma^D, W_\Delta^D, W_\gamma^D, W_\Gamma^D; \beta)$ which is the same loss explained in equation 5 computed for m steps ahead of the timestep t for learning the one or more parameters decoder network 118. The present disclosure then predicts outcome $\hat{\mathcal{Y}}_{t+m+1}$ for m+1 timesteps ahead of t as:

$$\hat{\mathcal{Y}}_{t+m+1} = W_\gamma^D([\Phi_\gamma^D(s_{t+m}), \Phi_\Delta^D(s_{t+m}), a_{t+m}]) \quad (7)$$

and proceed iteratively for all values of m up to τ−1 timesteps ahead of the timestep t. Further, it should be noted that the true $\mathcal{Y}_{t+m}$ is not available as input during test time for the decoder network 118. Hence, previous timestep's outcome predicted by decoder network 118 $\hat{\mathcal{Y}}_{t+m}$ is autoregressively used as input to the decoder network 118 which is represented in equation 6 for prediction of $\hat{\mathcal{Y}}_{t+m+1}$ (refer FIG. 4).

In the present disclosure, the experimental set-up used for measuring the performance/efficacy of the DRTCI system as implemented herein comprises of describing the dataset, followed by baselines, evaluation metrics and implementation specifics for evaluation of the DRTCI system. The present disclosure uses a bio-model (as known in the art) for simulating a lung cancer dataset which contains the outcomes for different treatment options including no treatment, chemotherapy, radiotherapy, and both chemotherapy and radiotherapy treatments on tumor growth volume in a longitudinal manner. In the present disclosure, the initial cancer stage and the initial tumor volume are obtained from prior distributions for each patient. The volume of the tumor t days after diagnosis is then obtained using the following mathematical model:

$$V(t+1) = \left(1 + \rho log\left(\frac{\kappa}{V(t)}\right) - \beta_c C(t) - (\alpha_r d(t) + \beta_r d(t)^2) + e(t)V(t)\right) \quad (8)$$

where κ, ρ, $\beta_c$, $\alpha_r$, $\beta_r$, e(t) are sampled as described in a known prior art (Geng, C., Paganetti, H., and Grassberger, C. Prediction of treatment response for combined chemo- and radiation therapy for non-small cell lung cancer patients using a bio-mathematical model. Scientific reports, 7(1):1-12, 2017). Further, time-varying confounding is introduced by modelling chemotherapy and radiotherapy assignment as Bernoulli random variables (known in the art) with probability of chemotherapy ($p_c$) and radiotherapy ($p_r$) depending upon the tumor volume:

$$p_c(t) = \left(\frac{\gamma_c}{D_{max}}(\bar{D}(t) - \delta_c)\right) \text{ and } p_r(t) = \left(\frac{\gamma_r}{D_{max}}(\bar{D}(t) - \delta_r)\right),$$

where $\gamma_c$, $\gamma_r$ are the factors controlling degree of time-varying confounding, $\bar{D}(t)$ is the average diameter over the last 15 days, $D_{max}$=13 cm, σ(•) is the sigmoid and $$\delta_r = \delta_c = \frac{D_{max}}{2}.$$

Chemotherapy concentration is given by $$C(t) = 5 + C\frac{(t-1)}{2}$$

and radiotherapy dose is d(t)=2 if applied at timestep t. In the present disclosure, a dataset for a maximum of 60 timesteps is generated and DRTCI system is evaluated under different degrees of time-dependent confounding ($\gamma_c$, $\gamma_r$) and time horizons (τ). For each setting of $\gamma_c$, $\gamma_r$, τ, the present disclosure simulated 10000 patients for training, 1000 for validation and 1000 for testing. For testing of next step ahead prediction using an encoder network 114, the present disclosure simulated volume V (t+1) for each timestep t under all treatment options for each patient while for T-step ahead prediction using the decoder, 2τ counterfactual sequences of outcomes with each sequence is generated giving chemotherapy at one of t, . . . t+τ−1 and similarly radiotherapy at one of t, . . . t+τ−1 timesteps for each timestep t in the patient's trajectory. The present disclosure benchmark the DRTCI system against Marginal Structural Models (MSMs) (as known in the art) which uses logistic regression for inverse propensity weighting and linear regression for prediction, Recurrent Marginal Structural Networks (RMSNs) (as known in the art) which uses a sequence-to-sequence architecture for handling confounders and outcome prediction and Counterfactual Recurrent Network (CRN) (as known in the art) which introduces adversarial balancing for handling confounders and outcome prediction. The performance of the DRTCI system has been measured/tested in terms of normalized root mean squared error % (NRMSE %) with NRMSE %=(RMSE/maximum tumor volume)*100, where $$RMSE = \left(\frac{\sum_k \sum_t (\hat{y}_{t+1} - y_{t+1})^2}{NT}\right)^{1/2}$$

for encoder, with $\mathcal{Y}_{t+1}$ replaced by $\mathcal{Y}_{t+\tau}$ for decoder error computation.

In an embodiment of the present disclosure, the DRTCI system has been evaluated by comparing the DRTCI system performance with baselines for varying degrees of time-varying confounding and for τ-step ahead counterfactual predictions. For instance, the present disclosure compared the DRTCI system for varying degrees of confounding including (a) $\gamma_c=\gamma_r=5$, (b) $\gamma_r=5$, $\gamma_c=0$, (c) $\gamma_r=0$, $\gamma_c=5$ with the baseline's approaches mentioned earlier. The present disclosure analyzed the comparison for x-step ahead counterfactual prediction with τ increasing in steps of 1 from 3 to 7 as depicted in Table 1. As evident from Table. 1, the DRTCI system substantially outperformed RMSN, MSM and the current state of art CRN for all different values of T and degree of confounding ($\gamma_r$, $\gamma_c$). The present disclosure further analyzed the performance of DRTCI system for very high degrees of confounding by setting $\gamma_r=\gamma_c=\gamma \in \{6, 7, 8, 9, 10\}$ for τ=1 (next step ahead prediction) and =3, and 5 as represented in Table. 2. The experimental results show that the DRTCI system performance for high confounding is superior to CRN (as known in the art) for next step ahead prediction and better by large margins for τ-step ahead prediction achieving more than 32% and 25% reduction in errors for τ=3 and τ=5 respectively. The achieved experimental results are able to obtain reduction in error since the proposed DRTCI system learns confounding representation which plays a significant role in the outcome prediction, especially when the degree of confounding is high, which is in contrast to known approaches where confounding covariates are balanced for reduction in bias and reliable outcome prediction. Moreover, while in known approaches a shared outcome regression arm would lead to noisy interference between the treatment predictions, whereas in the DRTCI system since only the relevant factors are being used to predict outcomes, noisy interference is greatly reduced, and common knowledge is better utilized across treatments.

TABLE 1

NRMSE % comparisons for (a) $\gamma_c = \gamma_r = 5$, (b) $\gamma_r = 5$, $\gamma_c = 0$, (c) $\gamma_r = 0$, $\gamma_c = 5$ $\tau$-step ahead prediction.

|     |       | T = 3 | T = 4 | T = 5 | T = 6 | T = 7 |
|-----|-------|-------|-------|-------|-------|-------|
| (a) | DRTCI | 2.01% | 2.66% | 3.00% | 2.81% | 2.14% |
|     | CRN   | 2.43% | 2.83% | 3.18% | 3.51% | 3.93% |
|     | RMSN  | 3.16% | 3.95% | 4.37% | 5.61% | 6.21% |
|     | MSM   | 6.75% | 7.65% | 7.95% | 8.19% | 8.52% |
| (b) | DRTCI | 1.11% | 1.81% | 2.03% | 2.23% | 2.43% |
|     | CRN   | 1.54% | 1.81% | 2.03% | 2.23% | 2.43% |
|     | RMSN  | 1.59% | 2.25% | 2.71% | 2.73% | 2.88% |
|     | MSM   | 3.23% | 3.52% | 3.63% | 3.71% | 3.79% |
| (c) | DRTCI | 1.31% | 1.16% | 1.31% | 1.21% | 1.31% |
|     | CRN   | 1.08% | 1.21% | 1.33% | 1.42% | 1.53% |
|     | RMSN  | 1.35% | 1.81% | 2.13% | 2.41% | 2.43% |
|     | MSM   | 3.68% | 3.84% | 3.91% | 3.97% | 4.04% |

TABLE 2

NRMSE % of DRTCI for high γ (high confounding)

|       | T = 1 |       | T = 5 |       | T = 5 |       |
|-------|-------|-------|-------|-------|-------|-------|
| Γ     | DRTCI | CRN   | DRTCI | CRN   | DRTCI | CRN   |
| 6     | 1.54% | 1.72% | 2.87% | 4.64% | 2.87% | 4.26% |
| 7     | 1.87% | 1.89% | 3.82% | 4.65% | 3.66% | 5.81% |
| 8     | 2.60% | 2.78% | 4.99% | 8.13% | 4.65% | 7.72% |
| 9     | 3.03% | 3.06% | 6.57% | 8.32% | 6.55% | 6.24% |
| 10    | 4.17% | 4.26% | 6.66% | 1.32% | 6.51% | 8.53% |
| Mean  | 2.64% | 2.74% | 4.98% | 7.41% | 4.85% | 6.51% |

In an embodiment, the present disclosure carried out an extensive ablation study to identify the key factors contributing towards the performance of the DRTCI system, wherein the study was performed for 5-step ahead prediction for varying degree of confounding with γ=3, 7, and 10. The present disclosure examined the conditions which includes $\Phi_\gamma$: DRTCI system with no disentangled representation but only $\Phi_\gamma$ as the representation layer, $\Phi_\gamma \oplus \Phi_\Delta$: DRTCI system with outcome representation $\Phi_\gamma(\bullet)$, the confounding representation $\Phi_\Delta(\bullet)$, and no separate representation for only the treatment representation $\Phi_\Gamma(\bullet)$, $\Phi_\gamma \oplus \Phi_\Gamma$: DRTCI system with the outcome representation $\Phi_\gamma(\bullet)$, the treatment representation $\Phi_\Gamma(\bullet)$ and no representation for confounding $\Phi_\Delta(\bullet)$ as depicted in Table 3. Further, by analyzing the representation layer which contributes most towards the performance, it was observed that the outcome representation (column $\Phi_\gamma$) alone does not provide significant performance gains while learning treatment or the confounding representation along with the outcome representation $\Phi_\gamma \oplus \Phi_\Delta$, $\Phi_\gamma \oplus \Phi_\Gamma$ gives a significant performance gain. Thus, the representations which retain confounding and treatment factors such as in the DRTCI system of the present disclosure, has the most significant impact on improvement of counterfactual prediction in longitudinal data, especially when the degree of confounding is high.

TABLE 3

Ablation Study for DRTCI $\tau$ = step ahead performance

| γ  | DRTCI | $\Phi_\gamma$ | $\Phi_\gamma \oplus \Phi_\Delta$ | $\Phi_\gamma \oplus \Phi_\Gamma$ | CRN   |
|----|-------|---------------|-----------------------------------|-----------------------------------|-------|
| 3  | 1.58% | 1.76%         | 1.56%                             | 1.56%                             | 1.72% |
| 7  | 3.66% | 5.02%         | 4.19%                             | 4.65%                             | 5.81% |
| 10 | 6.51% | 7.87%         | 6.97%                             | 6.61%                             | 8.53% |

Figure 5:
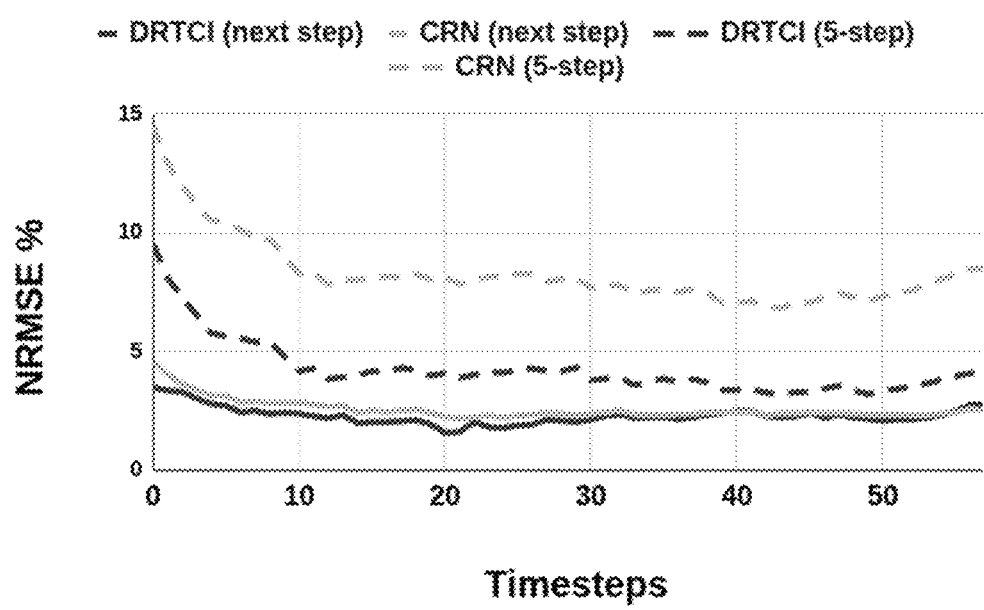
FIG. 5 illustrates the performance of the system and method for learning disentangled representations for temporal causal inference with high confounding of γ=8, in accordance with some embodiments of the present disclosure.

FIG. 5 illustrates a performance of the system and method for learning disentangled representations for temporal causal inference with high confounding of γ=8, in accordance with some embodiments of the present disclosure. The present disclosure evaluated the performance of the DRTCI system for next step ahead and 5-step ahead prediction for varying history sizes. The analysis for high confounding with γ=8 is depicted in FIG. 5. It can be observed that for next step prediction, the DRTCI system performed marginally better than CRN (known in the art) with minimal history, while for 5-step prediction the proposed DRTCI system performed significantly better for all history sizes.

Figure 6:
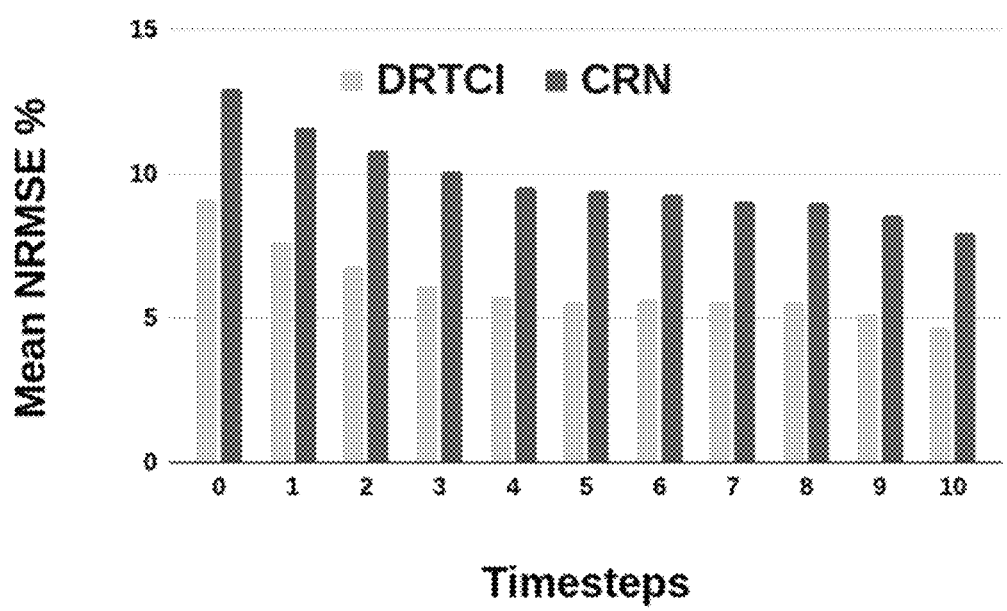
FIG. 6 illustrates the performance of the system and method for learning disentangled representations for temporal causal inference for early prediction using mean NRMSE % across γ for τ=5, in accordance with some embodiments of the present disclosure.

FIG. 6 illustrates the performance of the system and method for learning disentangled representations for temporal causal inference for early prediction using mean NRMSE % across γ for τ=5, in accordance with some embodiments of the present disclosure. The DRTCI system was analyzed for different history lengths as depicted in FIG. 6 using mean of NRMSE % values computed for high confounding. It can be seen that DRTCI system significantly outperformed CRN for early prediction and thus, when making distant early predictions in high confounding cases, the DRTCI system is more reliable.

Table 4 illustrates the search range of hyperparameters for encoder network 114 and decoder network 118 in the DRTCI system. The present disclosure selects optimal hyperparameters from the search space of hyperparameters, based on minimum NRMSE % in predicting the factual outcome for the validation dataset. Further, for evaluation of NRMSE %, the maximum tumor volume in the data is 1150 cm³. The present disclosure further uses a Tesla v100 with 4 GB GPU, 32 GB RAM for training and hyperparameter optimization for conducting the experiments.

TABLE 4

Encoder and decoder hyperparameter search space

| Hyperparameter | Encoder | Decoder |
| --- | --- | --- |
| Epochs | 100 | 50 |
| Batch Size | 256 | 1024 |
| Learning rate | 0.001 | 0.001 |
| MLP hidden units | 50, 100 | 50, 100 |
| Recurrent hidden units | 50, 100, 150 | Size of $\Psi_t$ |
| Dropout | 0.1 | 0.1 |
| β | 0.1, 0.4, 0.7, 1 | 0.1, 0.4, 0.7, 1 |

Table 5 illustrates the accuracy of treatment sequence prediction in conjunction with the system and method for learning disentangled representations for temporal causal inference. The present disclosure tested the treatment sequence prediction on 1000 patients with treatment sampled from $p_2s_t$ where $â_t \sim p_2s_t$ and evaluated using accuracy as metric for different degrees of confounding γ. It can be observed that for increasing γ accuracy of treatment prediction increases which is because, with increase in degree of confounding, factual treatment assignment is more biased and thus, easier to predict.

TABLE 5

Accuracy of treatment sequence prediction

| γ | Accuracy |
| --- | --- |
| 0 | 62% |
| 1 | 67.27% |
| 2 | 71.82% |
| 3 | 75.59% |
| 4 | 78.19% |
| 5 | 79.90% |
| 6 | 81.07% |
| 7 | 82.33% |
| 8 | 82.64% |
| 9 | 83.68% |
| 10 | 83.90% |

Hence, the present disclosure provides a system and method for learning disentangled representations for temporal causal inference. The present disclosure a DRTCI system to predict future treatment effects in a temporal setting with time-varying confounding. Further, the present disclosure demonstrated through experimental results that disentangling the recurrent hidden representations in the DRTCI system yielded substantial improvements to the prediction of future treatment effects over the recently proposed CRN model (as known in the art). The present disclosure further shows that the disentanglement is especially effective in situations with extreme confounding and is also beneficial for early prediction with less historical patient data. The present disclosure conducts ablation studies to determine which components of the proposed DRTCI system are contributing most to the improved performance and provide an analysis of the same.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method, comprising:
processing, via one or more hardware processors, a plurality of historical observants $h_t$ and treatment $a_t$ at a timestep t specific to each patient i using an encoder network, wherein the encoder network comprises of a recurrent network with an LSTM (Long short-term memory) unit, wherein the plurality of historical observants $h_t$ for each patient i is derived from an observational dataset $D=\{\{x_t^i, a_t^i, y_{t+1}^i\}_{t=1}^T \cup \{v^i\}\}_{i=1}^N$ for N patients containing a plurality of time dependent patient covariates $x_t^i$ for each patient i, the treatment $a_t^i$ received by each patient i, corresponding response $y_{t+1}^i$ to the treatment $a_t^i$ obtained from each patient i and a plurality of static covariates v for each patient i and wherein, the plurality of historical observants $h_t$ is represented by a sequence of the patient's time-varying covariates $\bar{x}_{1,t-1}=[x_1, \ldots, x_{t-1}]$, a sequence of treatments $\bar{a}_{1,t-1}=[a_1, \ldots, a_{t-1}]$ and the plurality of static covariates v as $h_t=[\bar{x}_{1,t-1}, \bar{a}_{1,t-1}, v]$;
obtaining, via the one or more hardware processors, a state representation $s_t$ using the processed plurality of historical observants $h_t$;
learning, via the one or more hardware processors, a first set of disentangled representations comprising an outcome representation ($\Phi_Y^E(s_t)$), a confounding representation ($\Phi_\Delta^E(s_t)$) and a treatment representation ($\Phi_\Gamma^E(s_t)$) by passing the obtained state representation $s_t$ at each timestep t through a plurality of disentangled-two-layered Exponential Linear Unit (ELU) Multi-Layer Perceptrons (MLPs) (306);
passing, via the one or more hardware processors, the outcome representation ($\Phi_Y^E(s_t)$), the confounding representation ($\Phi_\Delta^E(s_t)$) and the treatment $a_t$ through a set of layers ($W_Y^E$) comprising the plurality of disentangled-two-layered Exponential Linear Unit (ELU) Multi-Layer Perceptron's (MLPs) at the timestep t to predict an outcome $\hat{y}_{t+1}$ one timestep ahead of the timestep t;
concatenating, via the one or more hardware processors, the outcome representation ($\Phi_Y^E(s_t)$), the confounding representation ($\Phi_\Delta^E(s_t)$) and the treatment representation ($\Phi_\Gamma^E(s_t)$) from the encoder network to obtain a unified representation $\Psi_t$ for each timestep t for each patient i;
initializing, via the one or more hardware processors, a state of a decoder network comprising a LSTM (Long short-term memory) unit using the unified representation $\Psi_t$ to obtain a state representation $s_{t+m}$ specific to each patient i m-timestep ahead of the timestep t, wherein the decoder network is trained by splitting the observational dataset D of trajectory of each patient i into shorter sequences of τ timestep represented as $\{\{\Psi_t\} \cup \{\mathcal{Y}_{t+m}, a_{t+m}, \mathcal{Y}_{t+m+1}\}_{m=1}^{\tau-1} \cup \{v\}\}_{t=1}^{T-\tau}$ and wherein, $\mathcal{Y}_{t+m}$ denotes the predicted outcome m timestep ahead of the timestep t, $a_{t+m}$ denotes the treatment at each m timestep ahead of the timestep t and $\hat{y}_{t+m+1}$ denotes the predicted outcome m+1 timestep ahead of the timestep t;
learning, via the one or more hardware processors, a second set of disentangled representations comprising an outcome representation ($\Phi_Y^D(s_{t+m})$), a confounding representation ($\Phi_Y^D(s_{t+m})$) and a treatment representation ($\Phi_\Gamma^D(s_{t+m})$) by passing the obtained state representation $s_{t+m}$ for each m timestep ahead of the timestep t through the plurality of disentangled-two-layered Exponential Linear Unit (ELU) Multi-Layer Perceptron's (MLPs); and
concatenating, via the one or more hardware processors, the outcome representation ($\Phi_Y^D(s_{t+m})$), the confounding representation ($\Phi_\Delta^D(s_{t+m})$) and the treatment $a_{t+m}$ at each m timestep ahead of the timestep t and passing through a set of layers ($W_Y^D$) comprising the plurality of disentangled-two-layered Exponential Linear Unit (ELU) Multi-Layer Perceptron's (MLPs) to predict outcome $\hat{y}_{t+m+1}$ m+1 timesteps ahead of the timestep t and proceeding iteratively for all values of m up to τ−1 ahead of the timestep t.

2. The method of claim 1, wherein the encoder network further comprises of weights of LSTM unit, weights of Exponential Linear Unit (ELU) and weights of Multi-Layer Perceptron's (MLP's) wherein, weights of LSTM unit, weights of Exponential Linear Unit (ELU) and weights of Multi-Layer Perceptron's (MLP's) are used to compute a set of loss functions comprising a prediction loss, a treatment loss, an imbalance loss, and a weighting loss, and wherein, the set of loss functions are used to learn the first set of disentangled representations comprising the outcome representation ($\Phi_Y^E(s_t)$), the confounding representation ($\Phi_\Delta^E(s_t)$) and the treatment representation ($\Phi_\Gamma^E(s_t)$).

3. The method of claim 1, wherein the decoder network further comprises of weights of LSTM unit, weights of Exponential Linear Unit (ELU) and weights of Multi-Layer Perceptron's (MLP's), wherein, weights of LSTM unit, weights of Exponential Linear Unit (ELU) and weights of Multi-Layer Perceptron's (MLP's) are used to compute a set of loss functions comprising a prediction loss, a treatment loss, an imbalance loss, and a weighting loss, and wherein the set of loss functions are used to learn the second set of disentangled representations comprising the outcome representation ($\Phi_Y^D(s_{t+m})$), the confounding representation ($\Phi_\Delta^D(s_{t+m})$) and the treatment representation ($\Phi_\Gamma^D(s_{t+m})$).

4. The method of claim 1, further comprising processing a plurality of historical observants $h_t$ and treatment $a_t$ at a timestep t specific to a patient using the encoder network to obtain a state representation $s_t$.

5. The method of claim 4, further comprising initializing the state of the decoder network comprising the LSTM (Long short-term memory) unit using the unified representation $\Psi_t$ to obtain a state representation $s_{t+1}$ specific to the patient one timestep ahead of timestep t, wherein an input to the decoder network comprises the predicted outcome $\hat{y}_{t+1}$ one timestep ahead of the timestep t and treatment $a_{t+1}$ to obtain a predicted outcome $\hat{y}_{t+2}$, two timestep ahead of the timestep t, wherein the predicted outcome $\hat{y}_{t+2}$ serves as an input to the subsequent LSTM unit of the decoder network to predict an outcome $\hat{y}_{t+3}$ for the treatment $a_{t+2}$ and proceeding autoregressively till $\hat{y}_{t+\tau}$.

6. A system, comprising:
a memory storing instructions;
one or more communication interfaces; and
one or more hardware processors coupled to the memory via the one or more communication interfaces, wherein the one or more hardware processors are configured by the instructions to:
process a plurality of historical observants $h_t$ at a timestep t specific to each patient i using an encoder network, wherein the encoder network comprises of a recurrent network with an LSTM (Long short-term memory) unit, wherein the plurality of historical observants for each patient i is derived from an observational dataset $D=\{\{x_t^i, a_t^i, y_{t+1}^i\}_{t=1}^T \cup \{v^i\}\}_{i=1}^N$ for N patients containing a plurality of time dependent patient covariates $x_t^i$ for each patient i, the treatment $a_t^i$ received by each patient i, corresponding response $y_{t+1}^i$ to the treatment $a_t^i$ obtained from each patient i and a plurality of static covariates $v^i$ for each patient i and wherein, the plurality of historical observants $h_t$ is represented by a sequence of the patient's time-varying covariates $\bar{x}_{1,t-1}=[x_1, \ldots, x_{t-1}]$, a sequence of treatments $\bar{a}_{1,t-1}=[a_1, \ldots, a_{t-1}]$ and the plurality of static covariates v as $h_t=[\bar{x}_{1,t-1}, \bar{a}_{1,t-1}, v]$;
obtain a state representation $s_t$ using the processed plurality of historical observants $h_t$;
learn a first set of disentangled representations comprising an outcome representation ($\Phi_\gamma^E(s_t)$), a confounding representation ($\Phi_\Delta^E(s_t)$) and a treatment representation ($\Phi_\Gamma^E(s_t)$) by passing the obtained state representation $s_t$ at each timestep t through a plurality of disentangled-two-layered Exponential Linear Unit (ELU) Multi-Layer Perceptrons (MLPs);
pass the outcome representation ($\Phi_\gamma^E(s_t)$), the confounding representation ($\Phi_\Delta^E(s_t)$) and the treatment at through a set of layers ($W_\gamma^E$) comprising the plurality of disentangled-two-layered Exponential Linear Unit (ELU) Multi-Layer Perceptron's (MLPs) at the timestep t to predict an outcome $\hat{y}_{t+1}$ one timestep ahead of the timestep t;
concatenate the outcome representation ($\Phi_\gamma^E(s_t)$), the confounding representation ($\Phi_\Delta^E(s_t)$) and the treatment representation ($\Phi_\Gamma^E(s_t)$) from the encoder network to obtain a unified representation $\Psi_t$ for each timestep t for each patient i;
initialize a state of a decoder network comprising a LSTM (Long short-term memory) unit using the unified representation $\Psi_t$ to obtain a state representation $s_{t+m}$ specific to each patient i m-timestep ahead of the timestep t, wherein the decoder network is trained by splitting the observational dataset D of trajectory of each patient i into shorter sequences of $\tau$ timestep represented as $\{\{\Psi_t\} \cup \{y_{t+m}, a_{t+m}, y_{t+m+1}\}_{m=1}^{\tau-1} \cup \{v\}\}_{t=1}^{T-\tau}$ and wherein $y_{t+m}$ denotes the predicted outcome m timestep ahead of the timestep t, $a_{t+m}$ denotes the treatment at each m timestep ahead of the timestep t and $\hat{y}_{t+m+1}$ denotes the predicted outcome m+1 timestep ahead of the timestep t;
learn a second set of disentangled representations comprising an outcome representation ($\Phi_\gamma^D(s_{t+m})$), a confounding representation ($\Phi_\Delta^D(s_{t+m})$) and a treatment representation ($\Phi_\Gamma^D(s_{t+m})$) by passing the obtained state representation $s_{t+m}$ for each m timestep ahead of the timestep t through the plurality of disentangled-two-layered Exponential Linear Unit (ELU) Multi-Layer Perceptron's (MLPs); and
concatenate the outcome representation ($\Phi_\gamma^D(s_{t+m})$), the confounding representation ($\Phi_\Delta^D(s_{t+m})$) and the treatment $a_{t+m}$ at each m timestep ahead of timestep t and passing through a set of layers ($W_\gamma^D$) comprising the plurality of disentangled-two-layered Exponential Linear Unit (ELU) Multi-Layer Perceptron's (MLPs) to predict outcome $\hat{y}_{t+1+1}$ m+1 timesteps ahead of the timestep t and proceeding iteratively for all values of m up to $\tau-1$ ahead of the timestep t.

7. The system as claimed in claim 6, wherein the encoder network further comprises of weights of LSTM unit, weights of Exponential Linear Unit (ELU) and weights of Multi-Layer Perceptron's (MLP's) wherein, weights of LSTM unit, weights of Exponential Linear Unit (ELU) and weights of Multi-Layer Perceptron's (MLP's) are used to compute a set of loss functions comprising a prediction loss, a treatment loss, an imbalance loss, and a weighting loss, and wherein, the set of loss functions are used to learn the first set of disentangled representations comprising the outcome representation ($\Phi_\gamma^E(s_t)$), the confounding representation ($\Phi_\Delta^E(s_t)$) and the treatment representation ($\Phi_\Gamma^E(s_t)$).

8. The system as claimed in claim 6, wherein the decoder network further comprises of weights of LSTM unit, weights of Exponential Linear Unit (ELU) and weights of Multi-Layer Perceptron's (MLP's), wherein, weights of LSTM unit, weights of Exponential Linear Unit (ELU) and weights of Multi-Layer Perceptron's (MLP's) are used to compute a set of loss functions comprising a prediction loss, a treatment loss, an imbalance loss, and a weighting loss, and wherein, the set of loss functions are used to learn the second set of disentangled representations comprising the outcome representation ($\Phi_\gamma^D(s_{t+m})$), the confounding representation ($\Phi_\Delta^D(s_{t+m})$) and the treatment representation ($\Phi_\Gamma^D(s_{t+m})$).

9. The system as claimed in claim 6, wherein a plurality of historical observants $h_t$ and treatment $a_t$ are processed at a timestep t specific to a patient using the encoder network to obtain a state representation $s_t$.

10. The system as claimed in claim 9, wherein the state of the decoder network comprising the LSTM (Long short-term memory) unit is initialized using the unified representation $\Psi_t$ to obtain a state representation $s_{t+1}$ specific to the patient one timestep ahead of the timestep t, wherein an input to the decoder network comprises the predicted outcome $\hat{y}_{t+1}$ one timestep ahead of the timestep t and treatment $a_{t+1}$ to obtain a predicted outcome $\hat{y}_{t+2}$, two timestep ahead of the timestep t, wherein the predicted outcome $\hat{y}_{t+2}$ serves as an input to the subsequent LSTM unit of the decoder network to predict an outcome $\hat{y}_{t+3}$ for the treatment $a_{t+2}$ and proceeding autoregressively till $\hat{y}_{t+\tau}$.

11. One or more non-transitory machine-readable information storage mediums comprising one or more instructions which when executed by one or more hardware processors cause:
- processing a plurality of historical observants $h_t$ at a timestep t specific to each patient i using an encoder network, wherein the encoder network comprises of a recurrent network with an LSTM (Long short-term memory) unit, wherein the plurality of historical observants for each patient i is derived from an observational dataset $D=\{\{x_t^i, a_t^i, y_{t+1}^i\}_{t=1}^T \cup \{v^i\}\}_{i=1}^N$ for N patients containing a plurality of time dependent patient covariates $x_t^i$ for each patient i, the treatment $a_t^i$ received by each patient i, corresponding response $y_{t+1}^i$ to the treatment $a_t^i$ obtained from each patient i and a plurality of static covariates $v^i$ for each patient i and wherein, the plurality of historical observants $h_t$ is represented by a sequence of the patient's time-varying covariates $\bar{x}_{1,t-1}=[x_1, \ldots, x_{t-1}]$, a sequence of treatments $\bar{a}_{1,t-1}=[a_1, \ldots, a_{t-1}]$ and the plurality of static covariates v as $h_t=[\bar{x}_{1,t-1}, \bar{a}_{1,t-1}, v]$;
- obtaining a state representation $s_t$ using the processed plurality of historical observants $h_t$;
- learning a first set of disentangled representations comprising an outcome representation ($\Phi_Y^E(s_t)$), a confounding representation ($\Phi_\Delta^E(s_t)$) and a treatment representation ($\Phi_\Gamma^E(s_t)$) by passing the obtained state representation $s_t$ at each timestep t through a plurality of disentangled-two-layered Exponential Linear Unit (ELU) Multi-Layer Perceptrons (MLPs);
- passing the outcome representation ($\Phi_Y^E(s_t)$), the confounding representation ($\Phi_\Delta^E(s_t)$) and the treatment $a_t^i$ through a set of layers ($W_Y^E$) comprising the plurality of disentangled-two-layered Exponential Linear Unit (ELU) Multi-Layer Perceptron's (MLPs) at the timestep t to predict an outcome $\hat{y}_{t+1}$ one timestep ahead of the timestep t;
- concatenating the outcome representation ($\Phi_Y^E(s_t)$), the confounding representation ($\Phi_\Delta^E(s_t)$) and the treatment representation ($\Phi_\Gamma^E(s_t)$) from the encoder network to obtain a unified representation $\Psi_t$ for each timestep t for each patient i;
- initializing a state of a decoder network comprising a LSTM (Long short-term memory) unit using the unified representation $\Psi_t$ to obtain a state representation $s_{t+m}$ specific to each patient i m-timestep ahead of the timestep t, wherein the decoder network is trained by splitting the observational dataset D of trajectory of each patient i into shorter sequences of τ timestep represented as $\{\{\Psi_t\} \cup \{y_{t+m}, a_{t+m}, y_{t+m+1}\}_{m=1}^{\tau-1} \cup \{v\}\}_{t=1}^{T-\tau}$ and wherein $y_{t+m}$ denotes the predicted outcome m timestep ahead of the timestep t, $a_{t+m}$ denotes the treatment at each m timestep ahead of the timestep t and $\hat{y}_{t+m+1}$ denotes the predicted outcome m+1 timestep ahead of the timestep t;
- learning a second set of disentangled representations comprising an outcome representation ($\Phi_Y^D(s_{t+m})$), a confounding representation ($\Phi_\Delta^D(s_{t+m})$) and a treatment representation ($\Phi_\Gamma^D(s_{t+m})$) by passing the obtained state representation $s_t+m$ for each m timestep ahead of the timestep t through the plurality of disentangled-two-layered Exponential Linear Unit (ELU) Multi-Layer Perceptron's (MLPs); and
- concatenating the outcome representation ($\Phi_Y^D(s_{t+m})$), the confounding representation ($\Phi_\Delta^D(s_{t+m})$) and the treatment $a_{t+m}$ at each m timestep ahead of timestep t and passing through a set of layers ($W_Y^D$) comprising the plurality of disentangled-two-layered Exponential Linear Unit (ELU) Multi-Layer Perceptron's (MLPs) to predict outcome $\hat{y}_{t+m+1}$ m+1 timesteps ahead of the timestep t and proceeding iteratively for all values of m up to τ−1 ahead of the timestep t.

12. The one or more non-transitory machine readable information storage mediums of claim 11, wherein the encoder network further comprises of weights of LSTM unit, weights of Exponential Linear Unit (ELU) and weights of Multi-Layer Perceptron's (MLP's) wherein, weights of LSTM unit, weights of Exponential Linear Unit (ELU) and weights of Multi-Layer Perceptron's (MLP's) are used to compute a set of loss functions comprising a prediction loss, a treatment loss, an imbalance loss, and a weighting loss, and wherein, the set of loss functions are used to learn the first set of disentangled representations comprising the outcome representation ($\Phi_Y^E(s_t)$), the confounding representation ($\Phi_\Delta^E(s_t)$) and the treatment representation ($\Phi_\Gamma^E(s_t)$).

13. The one or more non-transitory machine readable information storage mediums of claim 11, wherein the decoder network further comprises of weights of LSTM unit, weights of Exponential Linear Unit (ELU) and weights of Multi-Layer Perceptron's (MLP's), wherein, weights of LSTM unit, weights of Exponential Linear Unit (ELU) and weights of Multi-Layer Perceptron's (MLP's) are used to compute a set of loss functions comprising a prediction loss, a treatment loss, an imbalance loss, and a weighting loss, and wherein the set of loss functions are used to learn the second set of disentangled representations comprising the outcome representation ($\Phi_Y^D(s_{t+m})$), the confounding representation ($\Phi_\Delta^D(s_{t+m})$) and the treatment representation ($\Phi_\Gamma^D(s_{t+m})$).

14. The one or more non-transitory machine readable information storage mediums of claim 11, wherein the one or more instructions which when executed by the one or more hardware processors cause processing a plurality of historical observants $h_t$ and treatment $a_t$ at a timestep t specific to a patient using the encoder network to obtain a state representation $s_t$.

15. The one or more non-transitory machine readable information storage mediums of claim 14, wherein the one or more instructions which when executed by the one or more hardware processors cause initializing the state of the decoder network comprising the LSTM (Long short-term memory) unit using the unified representation $\Psi_t$ to obtain a state representation $s_{t+1}$ specific to the patient one timestep ahead of timestep t, wherein an input to the decoder network comprises the predicted outcome $\hat{y}_{t+1}$ one timestep ahead of the timestep t and treatment $a_{t+1}$ to obtain a predicted outcome $\hat{y}_{t+2}$, two timestep ahead of the timestep t, wherein the predicted outcome $\hat{y}_{t+2}$ serves as an input to the subsequent LSTM unit of the decoder network to predict an outcome $\hat{y}_{t+3}$ for the treatment $a_{t+2}$ and proceeding autoregressively till $\hat{y}_{t+\tau}$.

* * * * *